United States Patent
Chen et al.

(10) Patent No.: US 9,766,187 B2
(45) Date of Patent: Sep. 19, 2017

(54) REPEATER DETECTION

(71) Applicant: KLA-Tencor Corporation, Milpitas, CA (US)

(72) Inventors: Hong Chen, San Ramon, CA (US); Kenong Wu, Davis, CA (US); Eugene Shifrin, Sunnyvale, CA (US); Masatoshi Yamaoka, Tokyo (JP); Gangadharan Sivaraman, Chennai (IN); Raghav Babulnath, San Jose, CA (US); Satya Kurada, Fremont, CA (US); Shuo Sun, Fremont, CA (US)

(73) Assignee: KLA-Tencor Corp., Milpitas, CA (US)

( * ) Notice: Subject to any disclaimer, the term of this patent is extended or adjusted under 35 U.S.C. 154(b) by 32 days.

(21) Appl. No.: 14/838,091

(22) Filed: Aug. 27, 2015

(65) Prior Publication Data
US 2016/0061745 A1 Mar. 3, 2016

Related U.S. Application Data (63) Continuation-in-part of application No. 14/674,856, filed on Mar. 31, 2015.
(Continued)

(51) Int. Cl.
*G01N 21/95* (2006.01)
*G01N 21/956* (2006.01)
*G01N 21/00* (2006.01)

(52) U.S. Cl.
CPC ... *G01N 21/9501* (2013.01); *G01N 21/95607* (2013.01); *G01N 21/00* (2013.01); *G01N 21/95* (2013.01)

(58) Field of Classification Search
USPC .... 356/237.1–241.6, 242.1–243.8, 426–431, 356/600–640
See application file for complete search history.

(56) References Cited

U.S. PATENT DOCUMENTS 4,644,172 A * 2/1987 Sandland ......... G01N 21/95607
250/548
5,808,735 A * 9/1998 Lee .................... G01N 21/9501
250/559.42
(Continued)

FOREIGN PATENT DOCUMENTS

| EP | 2195834 | 6/2010 |
|---|---|---|
| JP | 2004-177139 | 6/2004 |
| JP | 2008-014650 | 1/2008 |

OTHER PUBLICATIONS

International Search Report for PCT/US2015/047139 mailed Dec. 14, 2015.

*Primary Examiner* — Tri Ton
*Assistant Examiner* — Jarreas C Underwood
(74) *Attorney, Agent, or Firm* — Ann Marie Mewherter (57) ABSTRACT

Systems and methods for detecting defects on a wafer are provided. One method includes generating test image(s) for at least a portion of an array region in die(s) on a wafer from frame image(s) generated by scanning the wafer with an inspection system. The method also includes generating a reference image for cell(s) in the array region from frame images generated by the scanning of the wafer. In addition, the method includes determining difference image(s) for at least one cell in the at least the portion of the array region in the die(s) by subtracting the reference image from portion(s) of the test image(s) corresponding to the at least one cell. The method further includes detecting defects on the wafer in the at least one cell based on the difference image(s).

22 Claims, 5 Drawing Sheets

Related U.S. Application Data (60) Provisional application No. 62/042,251, filed on Aug. 27, 2014.

(56) References Cited

U.S. PATENT DOCUMENTS

| | | | | |
|---|---|---|---|---|
| 5,859,698 A * | 1/1999 | Chau | G01N 21/95607 | 356/237.2 |
| 5,864,394 A * | 1/1999 | Jordan, III | G01N 21/94 | 257/E21.53 |
| 5,917,588 A * | 6/1999 | Addiego | G01N 21/8806 | 356/237.2 |
| 6,031,607 A * | 2/2000 | Miyazaki | G06T 7/001 | 250/550 |
| 6,781,688 B2 * | 8/2004 | Kren | G01N 21/9501 | 356/237.1 |
| 7,127,098 B2 * | 10/2006 | Shimoda | G01N 21/95684 | 250/208.1 |
| 7,379,175 B1 * | 5/2008 | Stokowski | G01N 21/95607 | 356/237.5 |
| 7,440,607 B1 * | 10/2008 | Lin | G01N 21/8851 | 382/149 |
| 7,570,800 B2 | 8/2009 | Lin et al. | | |
| 7,664,608 B2 * | 2/2010 | Urano | G01N 21/4738 | 356/237.1 |
| 7,751,046 B2 * | 7/2010 | Levy | G01N 21/211 | 356/237.1 |
| 7,916,286 B2 * | 3/2011 | Sali | G01N 21/95607 | 356/237.1 |
| 8,000,922 B2 | 8/2011 | Chen et al. | | |
| 8,041,106 B2 | 10/2011 | Pak et al. | | |
| 8,103,087 B2 * | 1/2012 | Maeda | G06K 9/00557 | 348/25 |
| 8,111,900 B2 | 2/2012 | Wu et al. | | |
| 8,204,296 B2 | 6/2012 | Bhaskar et al. | | |
| 8,223,327 B2 | 7/2012 | Chen et al. | | |
| 8,467,047 B2 | 6/2013 | Chen et al. | | |
| 8,594,823 B2 | 11/2013 | Park et al. | | |
| 8,605,275 B2 | 12/2013 | Chen et al. | | |
| 8,692,878 B2 | 4/2014 | Chen et al. | | |
| 8,841,824 B2 * | 9/2014 | Ko | H01J 65/04 | 250/306 |
| 9,311,698 B2 * | 4/2016 | Chu | H01L 22/12 | |
| 2003/0001598 A1 * | 1/2003 | Weiner | G01R 31/307 | 324/754.22 |
| 2005/0232478 A1 * | 10/2005 | Onishi | G06T 7/0004 | 382/149 |
| 2006/0078191 A1 * | 4/2006 | Matsumura | G01N 21/8851 | 382/149 |
| 2007/0133860 A1 * | 6/2007 | Lin | G06T 7/001 | 382/149 |
| 2010/0021041 A1 | 1/2010 | Matsui et al. | | |
| 2012/0070089 A1 | 3/2012 | Yamada et al. | | |

* cited by examiner

REPEATER DETECTION

BACKGROUND OF THE INVENTION

1. Field of the Invention

The present invention generally relates to systems and methods for detecting defects on a wafer, which are particularly useful for detecting repeating defects in array regions on the wafer.

2. Description of the Related Art

The following description and examples are not admitted to be prior an by virtue of their inclusion in this section.

Inspection processes are used at various steps during a semiconductor manufacturing process to detect defects on wafers to promote higher yield in the manufacturing process and thus higher profits. Inspection has always been an important part of fabricating semiconductor devices such as IC's. However, as the dimensions of semiconductor devices decrease, inspection becomes even more important to the successful manufacture of acceptable semiconductor devices because smaller defects can cause the devices to fail.

Some current inspection methods use standard images such as standard die images to detect repeater defects on wafers. Repeater defects are normally caused by foreign objects on a reticle/mask. After a wafer is printed with this kind of reticle, the defect appears on all dies. A die-to-die comparison inspection will fail because the defects on all dies will cancel each other resulting in weak or no signal from the defect. A standard die image (also commonly referred to as a "golden die") may be compared to a test die image acquired for a wafer being inspected and the results of the comparison may be input to a defect detection algorithm or method to determine if any defects are present in the test die. Such golden die images are commonly used for inspection of logic regions of dies since the logic regions of dies often do not include periodically repeating features that can be compared to one another for defect detection.

A disadvantage of using a standard die image for inspection is that, if the standard die image was acquired from a wafer other than the one being inspected, wafer-to-wafer noise can be relatively high and can interfere with defect detection or decrease the sensitivity of defect detection. In addition, if the standard die image is acquired using the same wafer that is being inspected, die-to-die noise can also interfere with, or decrease sensitivity of, defect detection. Furthermore, if the standard die image is generated using design data for the wafer, the standard die image may not adequately represent noise sources on the wafer thereby having the same disadvantages described above.

Accordingly, it would be advantageous to develop systems and methods for detecting defects on a wafer that do not have one or more of the disadvantages described above.

SUMMARY OF THE INVENTION

The following description of various embodiments is not to be construed in any way as limiting the subject matter of the appended claims.

One embodiment relates to a computer-implemented method for detecting defects on a wafer. The method includes generating one or more test images for at least a portion of an array region in one or more dies on a wafer from one or more frame images generated by scanning the wafer with an inspection system. The method also includes generating a reference image for one or more cells in the array region from two or more of the frame images generated by the scanning of the wafer with the inspection system. In addition, the method includes determining one or more difference images for at least one cell in at least the portion of the array region in the one or more dies by subtracting the reference image from one or more portions of the one or more test images corresponding to the at least one cell. The method further includes detecting defects on the wafer in the at least one cell based on the one or more difference images determined for the at least one cell. Generating the one or more test images, generating the reference image, determining the one or more difference images, and detecting the defects are performed with a computer system.

Each of the steps of the method may be further performed as described herein. In addition, the method may include any other step(s) of any other method(s) described herein. Furthermore, the method may be performed by any of the systems described herein.

Another embodiment relates to a non-transitory computer-readable medium storing program instructions executable on a computer system for performing a computer-implemented method for detecting defects on a wafer. The computer-implemented method includes the steps of the method described above. The computer-readable medium may be further configured as described herein. The steps of the computer-implemented method may be performed as described further herein. In addition, the computer-implemented method for which the program instructions are executable may include any other step(s) of any other method(s) described herein.

An additional embodiment relates to a system configured to detect defects on a wafer. The system includes an inspection subsystem configured to scan a wafer to thereby generate frame images for the wafer. The system also includes a computer subsystem configured for performing the steps of the method described above. The system may be further configured as described herein.

BRIEF DESCRIPTION OF THE DRAWINGS

Further advantages of the present invention will become apparent to those skilled in the art with the benefit of the following detailed description of the preferred embodiments and upon reference to the accompanying drawings in which.

While the invention is susceptible to various modifications and alternative forms, specific embodiments thereof are shown by way of example in the drawings and are herein described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

The embodiments described herein relate to computer-implemented methods for detecting defects on a wafer. The embodiments described herein are particularly advantageous for detecting array repeater defects on wafers. In this manner, defect detection algorithm(s) that are configured to perform the method embodiments described herein may be referred to as array mode repeater algorithms. The term "array region" refers to the area in a die where the wafer pattern repeats periodically. The basic repeating pattern is called a "cell." Array regions are usually inspected by a cell-to-cell comparison instead of a die-to-die comparison. Die repeating defects may be detected at the same within die location in multiple frame images generated for different dies on the wafer. Die repeaters may be located in the array region of dies on the wafer. Due to severe noise in this region of the dies, array mode detection (commonly performed by cell-to-cell comparisons) does not have relatively high sensitivity for detecting the array repeaters. As will be described further herein, however, the embodiments described herein can be used to detect defects in the array region with higher sensitivity than that achievable by currently used systems and methods.

Figure 1:
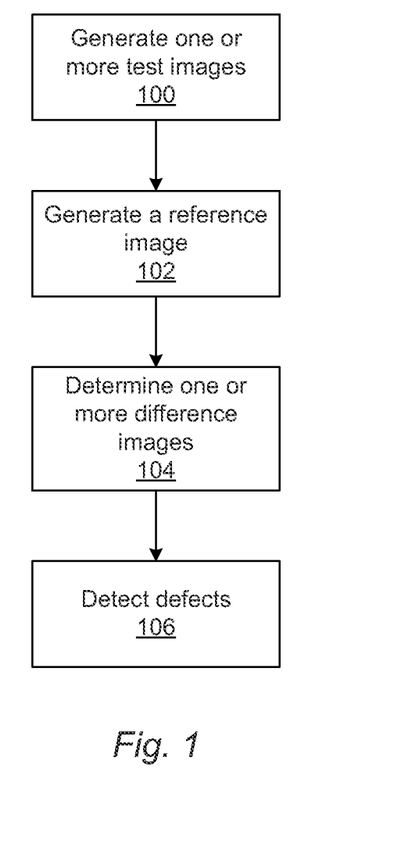
FIG. 1 is a flow chart illustrating one embodiment of a computer-implemented method for detecting defects on a wafer.

The method includes generating one or more test images, as shown in step 100 of FIG. 1, for at least a portion of an array region in one or more dies on a wafer from one or more frame images generated by scanning the wafer with an inspection system. The one or more dies may include any suitable number of dies on the wafer. For example, the one or more dies may include all of the dies in a row on the wafer, which may generally include from 3 or more dies. The array region in the one or more dies may have any suitable configuration known in the art and may be identified in the dies in any suitable manner (e.g., based on a design for the wafer and/or based on pattern characteristics in output (e.g., images) for the wafer). Scanning the wafer may be performed as described further herein with an inspection system that may be configured as described further herein. In addition, the method may include acquiring the frame images by performing such scanning of a wafer or may acquire the frame images from a storage medium in which the frame images were stored (e.g., by the inspection system that performed the scanning).

In one embodiment, generating the one or more test images is performed such that differences between portions of the one or more test images corresponding to defects and portions of the one or more test images corresponding to noise are greater than the differences in the one or more frame images. For instance, generating test image(s) as described further herein can enhance the signal (from die repeaters) to noise (random defects and other noise) ratio. In one such instance, as described further herein, generating the one or more test images includes performing a robust averaging of multiple frame images. Although some embodiments are described herein with respect to robust averaging, the embodiments are not limited to using such averaging to generate the images that are used as test images. For example, the test images may be generated using any method or algorithm that can enhance the die repeater signal as described above, which may include generating a median image or an average image from the frame images, which is then used as the test image. In this manner, the test image's include a die relative median image.

In one embodiment, generating the one or more test images includes determining a robust average image from two or more of the frame images. In general, a robust average may be generated by removing the pixels for one outlier and computing the average from the rest of the pixels. In some such embodiments, a detection job may include image frames from two or more dies in a row on a wafer. Therefore, generating the test image(s) may include using each of the image frames from all or some of the dies in a row on the wafer to generate an average test image. In this manner, generating the test image(s) may include determining a robust average of all input frames.

The robust average frame image may then be used to detect die repeaters as described further herein. Generating a robust average image as described herein enhances the die repeater signal. For example, robust averaging will generally reduce any signals that vary from die to die such as noise and signals from random defects while substantially maintaining any signals that are substantially the same from die to die such as signals from repeating defects. As such, the die repeater defect signal will be enhanced with respect to the random defect signals and noise that are present in each of the individual frames that are averaged. Therefore, using such an image as the test image for defect detection as described further herein increases the sensitivity of the defect detection.

In another embodiment, generating the one or more test images includes determining the one or more test images from two or more of the frame images, and the method includes aligning the two or more frame images to each other prior to generating the one or more test images. The method may therefore include frame-by-frame alignment followed by generating the test image(s) from the aligned frames. For example, for frame images that are acquired by scanning a row of dies on a wafer, the frame images may be aligned to one of the frame images that is acquired at the centermost die in the row. In this manner, all individual test frames may be aligned to the center test frame before generating the one or more test images as described herein (e.g., via averaging). In addition, all of the input images may be aligned to any other suitable common point (e.g., in a design for the wafer or on the wafer itself). Determining the one or more test images from two or more aligned frame images may be performed according to any of the embodiments described further herein.

Aligning the frame images prior to generating the test image(s) (e.g., by averaging) will increase the signal-to-noise ratio in the test image(s), which will produce higher signal-to-noise ratios in the difference image(s) determined as described herein. Since the difference image(s) are used as described further herein for defect detection, higher signal-to-noise ratios in the difference images will provide higher sensitivity for the defect detection.

In an additional embodiment, each of the one or more test images is generated from only one of the one or more frame images. For example, unlike some embodiments described above in which multiple frame images are used in combination to generate a single test image that is then used for defect detection, in some embodiments, the test images may simply include the frame images that were generated by the inspection system. In this manner, each of the test images used for other steps described herein may be generated from or correspond to only one of the frame images. In some such embodiments, the test images may include the frame images themselves. However, some processing (e.g., noise filtering) may be performed on the frame images, each of which can then be used as a test image in other steps described herein.

The method includes generating a reference image, as shown in step 102 of FIG. 1, for one or more cells in the array region from two or more of the frame images generated by the scanning of the wafer with the inspection system. Generating the reference image may be performed in a number of different manners as described herein, and the way in which the reference image is generated may vary depending on the image(s) that are used as the test image(s). The cell(s) in the array region may have any suitable configuration known in the art, and the cell(s) can be identified in the array region in any suitable manner (e.g., based on a design for the wafer or based on information about patterns formed in the dies on the wafer that can be determined from images of the wafer).

In one embodiment, generating the reference image for the one or more cells in the array region from the two or more frame images is performed such that portions of the two or more frame images corresponding to defects on the wafer are altered. In other words, some portions of the frame images that are responsive to defects on the wafer preferably look different in the reference image than in the frame images. The portions of the two or more flume images corresponding to the defects on the wafer are preferably altered such that signals or image data corresponding to all defects and all noise are substantially suppressed or minimized. For example, although some specific methods are described herein for generating a reference image (e.g., using a median of a robust average), the important features of these mathematical operations are that they can be used to substantially exclude outliers (defects) from the final reference image and substantially suppress random noise in the final reference image. Any other mathematical operation(s) (e.g., a robust harmonic average) that possesses these capabilities would work and might be useful in some cases.

In one embodiment in which generating the one or more test images includes determining a robust average image from two or more of the frame images, generating the reference image includes determining a median cell image from the robust average image. In this manner, the method may include determining a multiple cell median image from the robust average test image. As described above, generating a robust average test image will enhance the repeater defect signal with respect to random defect signals and noise in each of the test image frames. Therefore, random defects and noise may be substantially eliminated from the robust average test image. As such, the repeater defect signal in such a robust average test image will essentially be an outlier that can be removed from the robust average test image by generating a median image from the robust average test image. Consequently, signals from random defects and noise will be substantially suppressed in the reference image by the robust averaging used to generate the test image and signals from repeating defects will be substantially suppressed by taking the median of the robust averaged image. Such a median cell image will, therefore, make an excellent reference image for defect detection due to its substantially low noise and defect-free characteristics.

In an additional embodiment in which each of the one or more test images is generated from only one of the one or more frame images, generating the reference image includes determining a median cell image from at least one of the one or more frame images. For instance, for every frame image, a median cell image can be determined and used as the reference image. In particular, a reference image may be computed by a multiple cell median (or robust averaging) from only one test image (where the test image is computed by multiple die median (or robust averaging)) when that test image includes more than one (or many) cells. As described further herein, other mathematical operation(s) may also be used that can essentially remove defect information from the frame images.

In some embodiments, the one or more frame images used to generate the one or more test images and the two or more frame images used to generate the reference image are acquired in the same scan of the wafer performed during the scanning. In other words, all of the frame images used in the embodiments described herein to generate the test image(s) and the reference image may be acquired in only one scan of the wafer. Therefore, the embodiments described herein are different from some other wafer inspection methods that use standard reference dies (SRDs) because unlike those methods, which typically require two scans, the embodiments described herein may be performed using only one scan of a wafer. For example, some SRD-based methods include an SRD training scan and an SRD inspection scan. The training scan may be used to generate a standard reference from a known good wafer. The SRD inspection run then scans the wafer being inspected and compares the current scan image with the standard reference image generated during the SRD training scan. However, the embodiments described herein do not require any such SRD training scan. Instead, the embodiments described herein can scan a wafer once and perform defect detection using a single scan similar to die-to-die (random mode inspection) or cell-to-cell (array mode) inspection. For example, a robust average test such as that described herein and a reference image that is a multiple cell median image can be generated from the same wafer scan.

In another embodiment, at least one of the one or more frame images used to generate the one or more test images and at least one of the two or more frame images used to generate the reference image are acquired in the same scan of a single die on the wafer. For example, all of the frame images used to generate the test image(s) may be used to generate the reference image. In another example, at least some of the frame images used to generate the test image(s) may be used to generate the reference image. In this manner, images used to generate the test image(s) and the reference image may be acquired in the same die or dies on the wafer. In addition, images acquired in at least one die on the wafer may be used to generate both the test image(s) and the reference image. Therefore, the embodiments described herein are different from other methods that generate test images from a first portion of dies on a wafer and a reference image from a second portion of dies on the wafer that is different than the first portion. The embodiments are also different from other methods that generate test images from a die or dies on one wafer and a reference image from a die or dies on another wafer.

Using at least some images acquired in the same die or dies to generate both the test image(s) and the reference image is possible because generating the reference image as described herein results in suppression and/or elimination of repeater defect signals, random defect signals and noise in the resulting reference image. Using images from the same die or dies for both test image generation and reference image generation is advantageous because different scans are not required for generation of the test image(s) and the reference image, which increases the throughput of the inspection process as well as reduces the inspection system output that needs to be handled and processed by the inspection system. In addition, using at least some images acquired in the same die or dies may be particularly advantageous when there are variations across a wafer or wafers (e.g., process variations that cause color variations in the output of the inspection system) because in such situations, the variations may cause the reference image generated using an image of a die different from the die or dies used to generate the test image(s) to be a less than ideal reference image, which can then reduce the sensitivity of the inspection performed using the reference image. In contrast, since the embodiments described herein may use the same die or dies on the wafer for both test image generation and reference image generation, the wafer variation in the images used for both test image generation and reference image generation will be relatively low, which allows a particularly suitable reference image to be generated thereby enabling relatively sensitive inspection. Although it may be advantageous as described above to use the same die or dies for both test image generation and reference image generation, the embodiments described herein may also be performed such that the dies used for test image generation are different than e.g., mutually exclusive of) the dies used for reference image generation.

The method also includes determining one or more difference images, as shown in step 104 of FIG. 1, for at least one cell in at least the portion of the array region in the one or more dies by subtracting the reference image from one or more portions of the one or more test images corresponding to the at least one cell. Determining the one or more difference images may be performed using any of the test and reference images described herein. For example, in one embodiment, determining the difference image(s) may include comparing a robust average test image with a multiple cell median image to detect die repeaters on the wafer. Since the reference image may be generated as described herein for a cell on the wafer and since the reference image may be subtracted from portion(s) of test image(s) corresponding to a cell on the wafer, generating the difference image(s) as described herein involves a cell-to-cell comparison. In addition, since the difference image(s) are used for defect detection as described further herein, the defect detection methods and systems described herein may be generally referred to as cell-to-cell defect detection methods and systems.

In an additional embodiment in which each of the one or more test images is generated from only one of the one or more frame images, determining the one or more difference images is performed by subtracting the reference image from the one or more portions of each of the one or more test images. In such an embodiment, the reference image may be a median cell image as described further herein. For example, for every frame image, a difference image may be determined using the frame image and the median cell image. In this manner, the difference image(s) may be generated by subtracting the median cell image from each of the test images, each of which was generated from only one of the frame images. Therefore, difference images may be generated for every cell. In other words, a difference image may be separately generated for each cell resulting in a one-to-one correspondence between difference images and cells. This embodiment is different than some other embodiments described herein in which the difference image is generated by subtracting the reference image from a test image generated from multiple frame images and therefore multiple cells. In this manner, the test images can be used collectively (e.g., as in a robust average test image) or singly (e.g., as multiple frame images) to determine only one difference image or multiple difference images.

The method further includes detecting defects, as shown in step 106 of FIG. 1, on the wafer in the at least one cell based on the one or more difference images determined for the at least one cell. For example, array mode defect detection may be performed using any of the difference images described herein. Detecting the defects based on the one or more difference images may be performed using any suitable defect detection method(s) and/or algorithm(s) known in the art. For example, median intensity values determined from a reference image generated as described herein may be plotted as a function of difference values in the one or more difference images to thereby generate a two-dimensional (2D) scatter plot. Outliers in the scatter plot may then be identified as corresponding to potential defects on the wafer. Existing defect detection algorithms such as the multi-die auto-thresholding (MDAT) algorithm that is used on some inspection systems that are commercially available from KLA-Tencor, Milpitas, Calif., may be used to perform such defect detection using scatter plots. In another example, signals in the difference image(s) may be compared to a threshold, and signals above the threshold may be identified as corresponding to defects while signals below the threshold may not be identified as corresponding to defects. However, the embodiments described herein are not limited in the types of defect detection methods and/or algorithms that can be used with the difference images described herein. For instance, the difference images determined as described herein can be input to any defect detection algorithm that accepts a difference image as input.

In one embodiment, the defects that are detected include defects that repeat in different cells at substantially the same within die location in two or more of the dies on the wafer. Since the test image is generated by robust averaging performed using multiple frame images in multiple dies, the detected defects are common for all of these dies and, therefore, reported as repeater defects for all of these dies. In this manner, the embodiments described herein can be used to detect die repeater defects in the array region of the dies. Detecting such defects is normally substantially difficult due to the noise that is usually present in inspection system output for the array region of dies. However, as described further herein, generating the test image(s) as described herein can enhance the signal-to-noise ratio for repeating defects and generating the reference image as described herein can suppress the signals from all defects and noise on the wafer. Therefore, using such test and reference images for defect detection as described herein provides substantially high sensitivity for detecting repeating defects including those located in the array region. The embodiments described herein are, therefore, particularly suitable for use in array mode repeater defect detection.

In one embodiment, detecting the defects includes determining an additional difference image from two or more of the difference images and detecting the defects based on the additional difference image. In one such embodiment, determining the additional difference image includes determining a robust average image from the two or more difference images. For example, in the embodiments in which the frame images themselves are used as the test images and a median cell image is used as the reference image, a difference image can be determined for each cell and then a robust average of all of the difference images may be generated. That robust average of the difference images may then be input to a defect detection step as described further herein, and defect detection may be performed as described further herein.

In another such embodiment, determining the additional difference image includes aligning the two or more difference images to each other and determining the additional difference image based on the aligned two or more difference images. For example, in embodiments described herein in which a difference image is determined for each cell, all of the difference images (or at least two of the difference images) for all of the cells (or at least two of the cells) may be aligned to each other and then a robust average image may be determined from the aligned difference images. Aligning the difference images to each other may include aligning all of the difference images to a common point (e.g., in the design for the wafer or based on patterns in the output generated for the wafer by the inspection system). In this case, difference images are being aligned rather than input images. Difference images do not have relatively sharp edges since the cell structure is the common pattern that is present in the median image and test image, which results in lower alignment/interpolation noise of the robust average difference image (compared to alignment of test images) and improves the signal-to-noise ratio for defect detection.

In some embodiments, the method includes identifying one or more of the at least one cell in which the defects are located based on the one or more frame images. In another embodiment, the detected defects are potential defects on the wafer, and the method includes determining a defect attribute for each of the potential defects and determining which of the at least one cell contains actual repeating defects based on the determined defect attributes corresponding to the at least one cell. For example, the method may include a post-processing step that determines the repeater signal on each die to find out which die(s) has or have the die repeater defect. In other words, the method may include computing a defect attribute for each repeater defect to indicate repeater signal from the frame images and reference images. The repeater signal value can be represented by a defect attribute. In one such example, the defect attribute calculation may include post-processing the defect patch on each frame from the dies included in a detection job to measure the repeater signal to determine whether the defect exists on each frame. Dies that have relatively strong signals at the identified repeater defect location may be identified as containing the repeater defect while dies that have relatively weak signals at the identified repeater defect location may be identified as not containing the repeater defect.

Generating the one or more test images, generating the reference image, determining the one or more difference images, and detecting the defects are performed with a computer system, which may be configured according to any of the embodiments described herein.

Each of the embodiments of the methods described above may include any other step(s) of any other method(s) described herein. Furthermore, each of the embodiments of the methods described above may be performed by any of the systems described herein.

All of the methods described herein may include storing results of one or more steps of the method embodiments in a computer-readable storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc.

Figure 2:
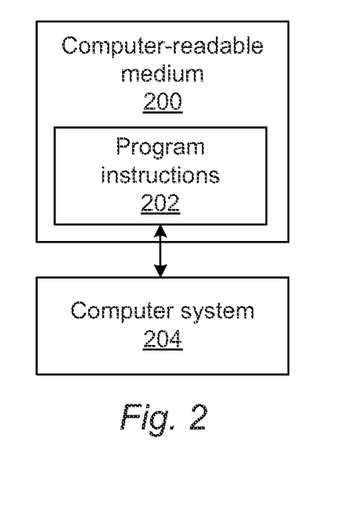
FIG. 2 is a block diagram illustrating one embodiment of a non-transitory computer-readable medium storing program instructions for causing a computer system to perform a computer-implemented method described herein.

Another embodiment relates to a non-transitory computer-readable medium storing program instructions executable on a computer system for performing a computer-implemented method for detecting defects on a wafer. One such embodiment is shown in FIG. 2. For example, as shown in FIG. 2, non-transitory computer-readable medium 200 stores program instructions 202 executable on computer system 204 for performing a computer-implemented method for detecting defects on a wafer. The computer-implemented method may include any step(s) of any method(s) described herein.

Program instructions 202 implementing methods such as those described herein may be stored on non-transitory computer-readable medium 200. The computer-readable medium may be a storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using Matlab, Visual Basic, ActiveX controls, C, C++ objects, C#, JavaBeans, Microsoft Foundation Classes ("MFC"), or other technologies or methodologies, as desired.

Computer system 204 may take various forms, including a personal computer system, mainframe computer system, workstation, system computer, image computer, programmable image computer, parallel processor, or any other device known in the art. In general, the term "computer system" may be broadly defined to encompass any device having one or more processors, which executes instructions from a memory medium.

Figure 3:
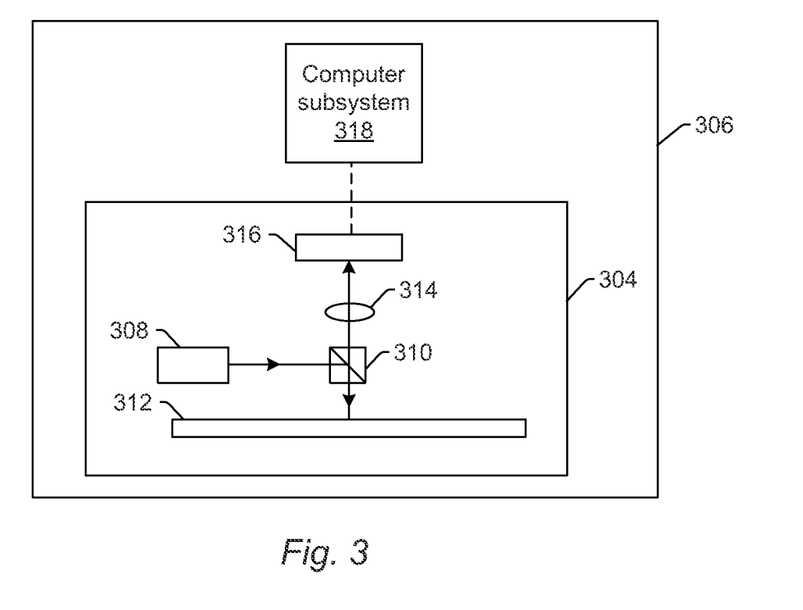
FIG. 3 is a schematic diagram illustrating a side view of an embodiment of a system configured to detect defects on a wafer.

An additional embodiment relates to a system configured to detect defects on a wafer. The system includes an inspection subsystem configured to scan a wafer to thereby generate frame images for the wafer. One embodiment of such an inspection subsystem is shown in FIG. 3 as inspection subsystem 304 of system 306. The inspection subsystem is configured to scan the wafer by scanning the wafer with light and detecting light from the wafer during the scanning. For example, as shown in FIG. 3, the inspection subsystem includes light source 308, which may include any suitable light source known in the art such as a broadband plasma light source.

Light from the light source may be directed to beam splitter 310, which may be configured to direct the light from the light source to wafer 312. The light source may be coupled to any other suitable elements (not shown) such as one or more condensing lenses, collimating lenses, relay lenses, objective lenses, apertures, spectral filters, polarizing components and the like. As shown in FIG. 3, the light may be directed to the wafer at a normal angle of incidence. However, the light may be directed to the wafer at any suitable angle of incidence including near normal and oblique incidence. In addition, the light or multiple light beams may be directed to the wafer at more than one angle of incidence sequentially or simultaneously. The inspection subsystem may be configured to scan the light over the wafer in any suitable manner.

Light from wafer 312 may be collected and detected by one or more detectors of the inspection subsystem during scanning. For example, light reflected from wafer 312 at angles relatively close to normal (i.e., specularly reflected light when the incidence is normal) may pass through beam splitter 310 to lens 314. Lens 314 may include a refractive optical element as shown in FIG. 3. In addition, lens 314 may include one or more refractive optical elements and/or one or more reflective optical elements. Light collected by lens 314 may be focused to detector 316. Detector 316 may include any suitable detector known in the art such as a charge coupled device (CCD) or another type of imaging detector. Detector 316 is configured to generate output that is responsive to the reflected tight collected by lens 314. Therefore, lens 314 and detector 316 form one channel of the inspection subsystem. This channel of the inspection subsystem may include any other suitable optical components (not shown) known in the art. The output of the detector may include, for example, images, image data, signals, image signals, or any other output that can be generated by a detector suitable for use in an inspection system.

Since the inspection subsystem shown in FIG. 3 is configured to detect tight specularly reflected from the wafer, the inspection subsystem is configured as a bright field (BF) inspection system. Such an inspection subsystem may, however, also be configured for other types of wafer inspection. For example, the inspection subsystem shown in FIG. 3 may also include one or more other channels (not shown). The other channel(s) may include any of the optical components described herein such as a lens and a detector, configured as a scattered light channel. The lens and the detector may be further configured as described herein. In this manner, the inspection subsystem may also be configured for dark field (DF) inspection.

The system also includes computer subsystem 318 that is coupled to the inspection subsystem such that the computer subsystem can receive frame images generated by the inspection subsystem. For example, the computer subsystem may be coupled to detector 316 and any other detectors included in the inspection subsystem such that the computer subsystem can receive frame image output generated by the detector(s). The computer subsystem is configured to perform the steps of the methods described herein including generating one or more test images, generating a reference image, determining one or more difference images, and detecting defects, according to any of the embodiments described herein. Computer subsystem 318 may be configured to perform any other steps described herein. The system shown in FIG. 3 may also be configured to perform any other steps described herein. The computer subsystem and the system may be further configured as described herein.

It is noted that FIG. 3 is provided herein to generally illustrate a configuration of an inspection subsystem that may be included in the system embodiments described herein. Obviously, the inspection subsystem configuration described herein may be altered to optimize the performance of the inspection subsystem as is normally performed when designing a commercial inspection system. In addition, the systems described herein may be implemented using an existing inspection subsystem (e.g., by adding functionality described herein to an existing inspection system) such as the 29xx/28xx series of tools that are commercially available from KLA-Tencor, Milpitas, Calif. For some such systems, the methods described herein may be provided as optional functionality of the system (e.g., in addition to other functionality of the system). Alternatively, the system described herein may be designed "from scratch" to provide a completely new system.

Furthermore, although the system is described herein as being an optical or light-based inspection system, the inspection subsystem may be configured as an electron beam based inspection subsystem. The electron beam based inspection subsystem may be any suitable electron beam based inspection subsystem included in any suitable commercially available electron beam inspection system.

Additional embodiments described herein relate to new methods and systems for maximizing repeater defect detection in array using inspection systems such as the broadband plasma (BBP) tools described further herein. For example, as described further herein, in one embodiment, the inspection subsystem (e.g., inspection subsystem 304 shown in FIG. 3) includes a light source (e.g., light source 308) configured to generate light that is scanned over the wafer (e.g., wafer 312), and the light source includes a BBP tight source. In another embodiment, the inspection subsystem is configured as a BF tool, and such configurations are described further herein.

In many semiconductor fabrication facilities, users of inspection tools monitor the quality of their masks used in a scanner for the presence of reticle haze. If the haze grows bigger than a critical size, it can manifest as a repeating defect on the wafer and users typically monitor the number of repeating events on the wafer and use this information to monitor reticle haze. For example, users may run a substantially hot inspection and then use wafer post-processing approaches for just separating the repeaters based on whether they appear in n number of dies or n number of reticle fields using a traditional repeater analysis method. In one such example, the inspection may produce a wafer map with millions of defects and then post-processing analysis may be used on this data to extract the required repeaters.

In this manner, the currently used methods truly include running a substantially hot scan for the best known mode (BKM) find all known repeaters in one or more reticle rows or die rows. The methods may also include determining the thresholds that enable finding all repeating defects. Based on the determined thresholds, a full wafer scan is performed, which can often produce a wafer map with millions of defects. (Sometimes, a scan can stop if defect count limits have been exceeded or the tool can miss defects because of not being able to handle as many defects as are being detected. After the full wafer scans are completed, the user may enable an automatic repeater analysis in wafer post-processing to extract the repeating defects.

Figure 4:
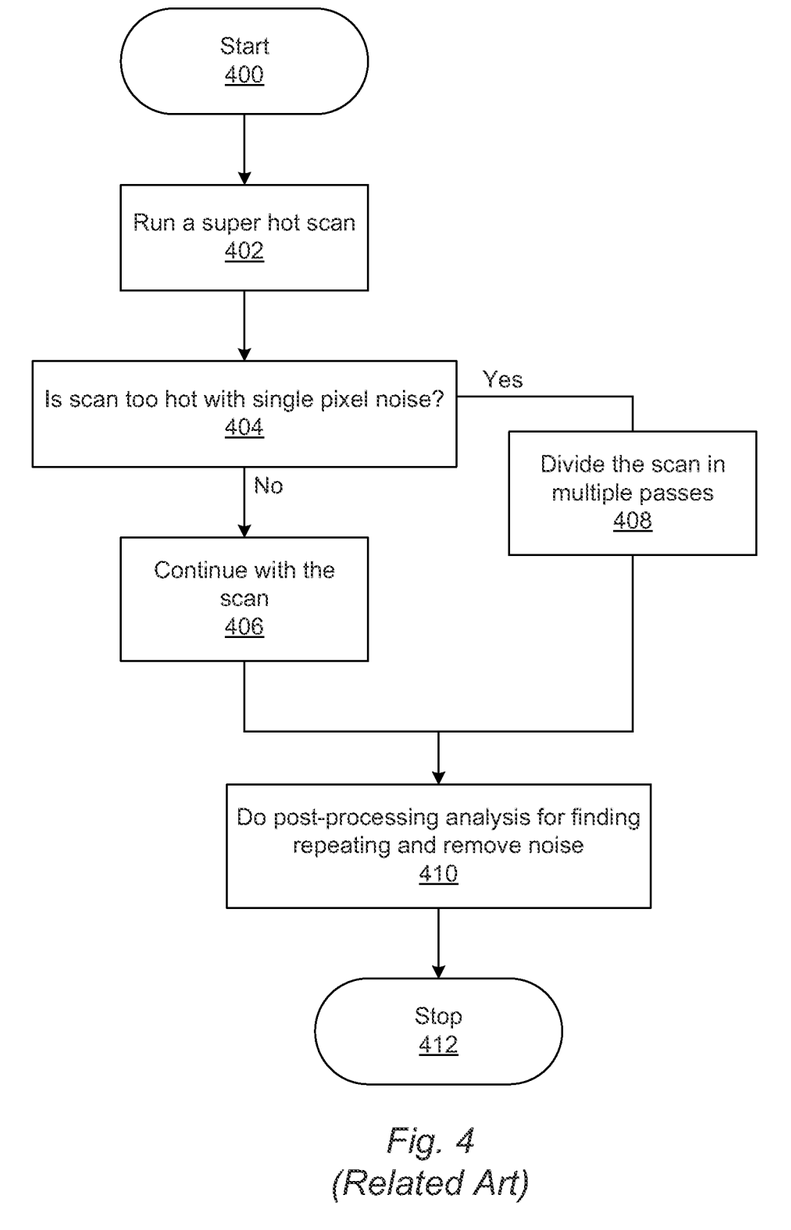
FIG. 4 is a flow chart illustrating one currently used method for detecting defects on a wafer.

FIG. 4 illustrates one currently used method for finding repeaters. The method starts at start 400 and then, in step 402, a "super" hot scan is run. A "super" hot scan can be defined as a scan in which defect detection is performed using a threshold that is at the noise floor of output produced during the scan (e.g., by one or more detectors). A threshold that is "at" the noise floor of the output may be generally defined as a threshold that is approximately equal to an average or mean of the noise floor. Therefore, such a threshold and super hot scan will result in a substantial amount of noise being detected on the wafer as potential defects. The method also includes determining if the scan is too hot with single pixel noise in step 404. For example, the method may include determining if too many noise or nuisance events have been detected by the scan. If the scan is not determined to be too hot, the method may include continuing with the scan, as shown in step 406. If the scan is determined to be too hot, the method may include dividing the scan in multiple passes, as shown in step 408. After scan(s) performed in steps 404 and 406 or 408, the method includes performing post-processing analysis for finding repeating defects and removing noise, as shown in step 410. The method may then stop as shown in step 412.

Currently used methods for monitoring reticle haze are disadvantageous because they can be unable to handle single pixel system noise when super hot inspections are run for detecting these repeating defects. For example, wafer defect counts can reach substantially high counts, which can make it substantially difficult to manage the inspection results while trying to detect these relatively small repeating defects. In addition, while running extremely hot inspections, the computer subsystem of the inspection tool can drop defects. If the inspection tool drops defects, key repeating defects of interest might not be detected because the inspection tool can drop repeating defects while trying to retain some single pixel noise. Furthermore, the system may be unable to complete a full wafer inspection if the inspection tool is stretched beyond its defect detection limits by running extremely hot scans. Moreover, if running the scans in multiple passes is required, such scans are disadvantageous over a single scan for a number of obvious reasons.

The embodiments described herein primarily enhance the detection of repeaters when running array mode inspection for detecting repeaters in the array region. These repeating defects (if printed) are going to be printed in every die and/or reticle field, and the challenge is the signal for some of the smallest repeating defects will be extremely low such that a substantially hot inspection has to be run, which results in the detection of a substantial amount of single pixel system noise, which requires post-processing such as repeater analysis to remove the nuisance events that are detected. In addition, sometimes, a full wafer inspection may not be able to be completed for extremely hot inspections performed to pull the repeating defects out of the noise floor.

The embodiments described herein may be generally referred to as die fusion or reticle fusion for BF-based inspection tools to enhance the detection of repeater defects by using the fact that the repeaters are going to be present in all of the dies in the same location and the nuisance events will not have this characteristic. The embodiments retain the defects only printed on adjacent dies by fusing the test and one or more reference images thereby using the fused information to retain defects printed on the same location in all dies whose images are being fused and throwing away defects that are not present in all dies. In this manner, in one embodiment, the defects include repeating defects. Therefore, such detection would not work for enhancing the detection of random, non-repeating defects as the idea requires the defect to be repeating in all dies.

Figure 5:
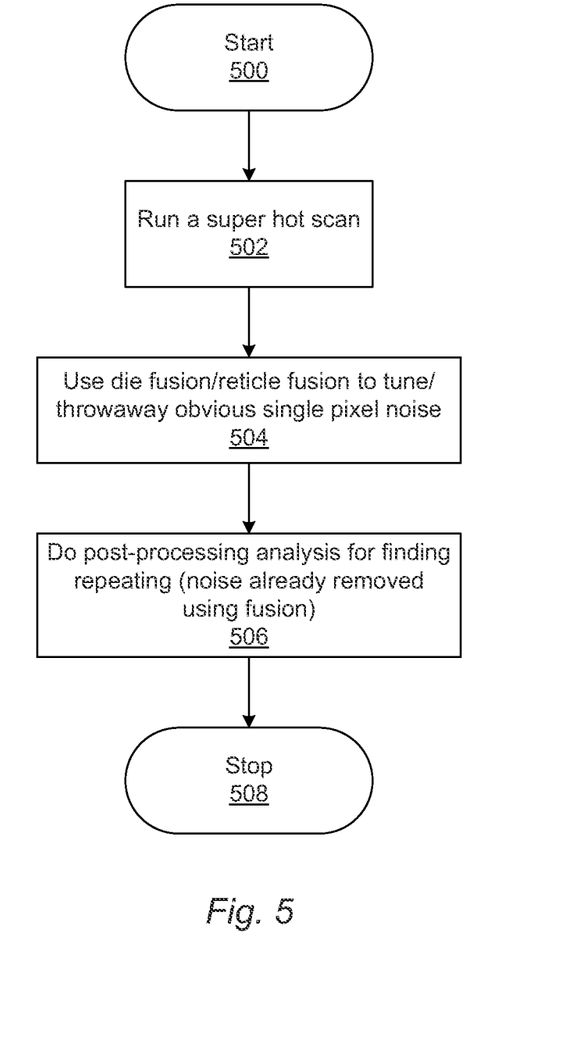
FIG. 5 is a flow chart illustrating one embodiment of a method for detecting defects on a wafer.

In one embodiment, the embodiments described herein include performing a substantially hot scan for a wafer using the BKM to find all known repeaters in one or more reticle rows or die rows. For example, in one embodiment, detecting the defects is performed using a predetermined threshold at a noise floor of output of a detector of the inspection subsystem. The predetermined threshold may be "at" the noise floor as described further above. In one such example, as shown in FIG. 5, the method may start at step 500 and then include running a super hot scan, as shown in step 502. When running such a substantially hot scan, the embodiments may include fusing images between adjacent dies and retaining all fused locations as they could possibly be a repeating event and/or repeating defect. For example, as shown in FIG. 5, the method may include using die fusion/reticle fusion to tune/throwaway obvious single pixel noise, in step 504. In this manner, obvious single pixel noise events can be thrown away in line. Throwing away obviously single pixel noise events in line makes it easier to handle the lot results. In addition, chances of defects getting dropped are reduced as the obvious noisy pixels are thrown away in-line.

In some embodiments, the fusion occurs at the image or detector output level. For example, in one embodiment, generating the one or more test images includes combining at least two of the frame images corresponding to substantially the same locations in the one or more dies thereby creating additional image data for the wafer, and the additional image data is used as the one or more test images in the determining the one or more difference images. Combining the at least two frame images may be performed as described further herein. For example, combining the at least two frame images may include generating an average or robust average of the at least two frame images to thereby create the additional image data. That additional image data may be used as described further herein to determine the difference image(s). Fusing the image data may also or alternatively be performed as described in U.S. Pat. No. 8,223,327 to Chen et al. issued on Jul. 17, 2012, U.S. Pat. No. 8,467,047 to Chen et al. issued on Jun. 18, 2013, and U.S. Pat. No. 8,605,275 to Chen et al, issued on Dec. 10, 2013, which are incorporated by reference as if fully set forth herein. The embodiments described herein may be further configured as described in these patents and may be configured to perform any step(s) of any method(s) described in these patents.

In one such embodiment, the at least two of the frame images include images of at least two of the one or more dies. In another embodiment, the at least two of the frame images include images of at least two reticle fields printed on the wafer. For example, the image fusion described above can be performed at the die or reticle field level.

In other embodiments, the fusion occurs using the identified potential defects. For example, one embodiment of a system configured to detect defects on a wafer includes an inspection subsystem configured to scan a wafer to thereby generate images for the wafer. Such an inspection subsystem may be further configured as described herein.

The system also includes a computer subsystem configured for, while the inspection subsystem is scanning the wafer, detecting potential defects on the wafer by applying a predetermined threshold to the images. The predetermined threshold is at a noise floor of output of a detector of the inspection subsystem. In this manner, the computer subsystem may be configured to detect the potential defects by performing a hot scan on the wafer. The predetermined threshold may be "at" the noise floor of the output as described further herein.

In addition, the computer subsystem is configured for, while the inspection subsystem is scanning the wafer, combining results of the detecting corresponding to substantially the same locations in two or more dies or two or more reticle fields on the wafer. For example, the results that are compared may include whether or not a potential defect was detected at the substantially the same locations in two or more dies or two or more reticle fields. In one embodiment, the combining is performed for only array regions of the two or more dies or the two or more reticle fields. For example, the embodiments described herein may be particularly suitable for inspection of the array regions of wafers. Other inspections such as those described further herein may be performed for other regions of the wafers.

The computer subsystem is also configured for, while the inspection subsystem is scanning the wafer, identifying one set of the potential defects that is detected at all of the substantially the same locations as repeating defects. For example, when the computer subsystem determines that a potential defect has been detected at all instances of the same location in two or more dies or reticle fields, all of the defects at each of the instances of that same location may be identified as repeating defects. In this manner, all of the repeating defects detected on the wafer can be separated into one set. In one embodiment, the repeating defects include two or more defects formed on the wafer due to haze on a reticle used to print the wafer. For example, as described further herein, the embodiments described herein are particularly advantageous for detecting defects on a wafer due to reticle haze.

The computer subsystem is further configured for, while the inspection subsystem is scanning the wafer, identifying another set of the potential defects that is detected at fewer than all of the substantially the same locations as non-repeating defects. For example, when the computer subsystem determines that a potential defect has not been detected at all instances of the same location in two or more dies or reticle fields, all of the defects at each of the instances of that same location may be identified as non-repeating defects. In this manner, all of the non-repeating defects detected on the wafer can be separated into another set that is different than the one including the repeating defects. As such, the repeating defects can be separated from the non-repeating defects in line.

The computer subsystem is also configured for generating inspection results for the wafer that include information for at least the repeating defects. For example, generating the inspection results may include excluding information for the non-repeating defects from the inspection results, e.g., by discarding any information for the non-repeating defects. In another example, generating the inspection results may include storing information for the repeating defects separately from the information for the non-repeating defects. In one such example, the information for the non-repeating defects may be stored separately from the repeating defects in the same file or in different files. In this manner, the information for the non-repeating defects may or may not be available after inspection of the wafer.

In some instances, it may be desirable to not discard all of the information for the non-repeating defects such that that information is available for other functions. For example, in one embodiment, the computer subsystem is configured for applying a nuisance filter to the non-repeating defects to identify at least one of the non-repeating defects that is an actual defect and at least one other of the non-repeating defects that is a nuisance. In this manner, for locations where perfect fusion did not occur, the locations may be passed through a nuisance fitter, which may include any suitable nuisance filter and/or defect classification method and/or algorithm, to retain the obvious real events and throw away all single pixel noise events. For example, as shown in FIG. 5, the method may include performing post-processing analysis for finding repeating (noise already removed using fusion), as shown in step 506, after which the method may stop as shown in step 508. The embodiments give the user the flexibility to be able to run a super hot scan as required to be able to detect the required repeating events and also give the user the flexibility of fusing adjacent die images and be able to throw away unwanted noise events by means of fusing.

The computer subsystem is also configured for determining if the repeating defects are due to haze on a reticle used to print the wafer in some embodiments. For example, the computer subsystem of the systems described herein may be configured to use information about the reticle (e.g., results of inspection of the reticle that may be performed after the defects were detected by the computer subsystem), other wafers printed using the reticle (e.g., wafer inspection results previously generated for the other wafers), and any other information that is available to the computer subsystem to determine if the repeating defects are due to haze on the reticle or are due to another cause.

The embodiments described herein advantageously allow existing inspection tools to enhance the repeater defect detection capability and allow tool users to monitor for reticle haze with an improved/better way for monitoring the repeating defects, and this new approach of finding repeating defects may be a key feature that will enhance the performance of existing inspection tools in finding repeating defects when extreme ultraviolet (EUV) (e.g., for 1.0 nm/7 nm logic) is introduced. In addition, the embodiments described herein extend substantially small repeater defect detection capabilities when extremely hot scans are run and yet produce successful results while not being required to have extremely hot lot results that are extremely tough to work through by giving the user an option to throw away unwanted noise by means of fusing adjacent die images. Furthermore, having a reasonably small lot result is often substantially easy to work with for further analysis. Moreover, recipes for the embodiments described herein can be seamlessly integrated into a production environment as die and/or reticle fusion provides a way to manage single pixel noise events. In addition, when running a hot scan, tools can sometimes choke and drop defects, and this scenario can possibly be avoided by using this approach.

Further embodiments described herein relate to using a robust average image of a reticle to improve sensitivity of reticle defect detection in logic areas (which may be referred to as repeater in random or (RIR)). For example, EUV technology is approaching production usage. Due to the vacuum environment of EUV scanners and exposure to shorter wavelengths, contamination control especially particle control is substantially critical EUV technology will be adopted on 10 nm and beyond logic devices and 1 znm DRAM devices. Therefore, sensitivity requirements are substantially high. Currently used inspection methodology cannot meet EUV reticle monitor sensitivity requirements in logic regions in order to monitor it on wafers. The embodiments described herein can be used, however, to extend the sensitivity capability of BBP pattern inspection tools with minimum cost to achieve these sensitivities.

Figure 6:
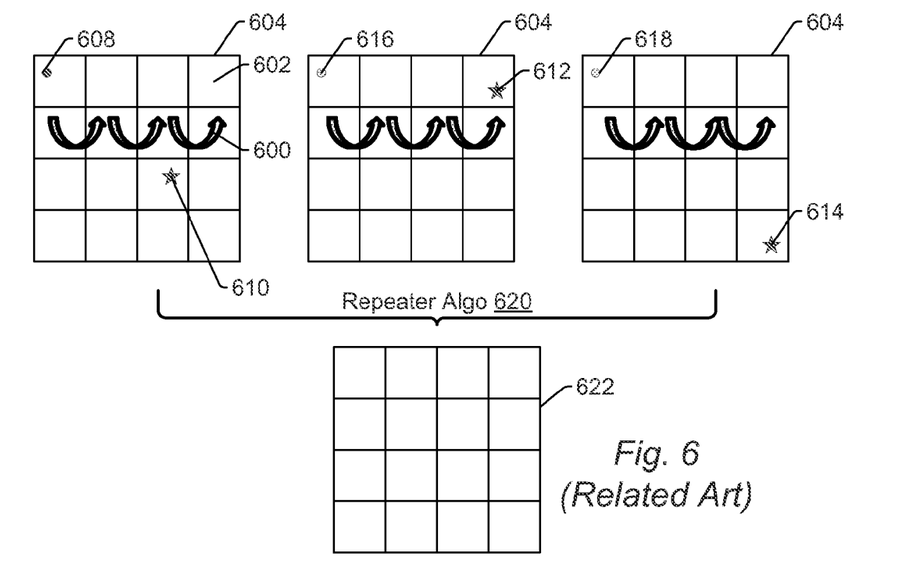
FIG. 6 is a schematic diagram illustrating one currently used method for detecting defects on a wafer.

In particular, currently used methods miss smaller and/or lower signal repeaters. For example, as shown in FIG. 6, current inspection may involve die-to-die comparisons 600 in which the images or other detector output are compared for different dies 602 in the same reticle field 604. Such comparisons may be preformed for each reticle field formed on a wafer (not shown in FIG. 6). Such die-to-die comparisons may detect defects 608, 610, 612, and 614. As shown in FIG. 6, defects 610, 612, and 614 are random defects in that two or more defects are not present in substantially the same location in multiple dies or reticle fields for any of these defects. However, as further shown in FIG. 6, defects 616 and 618 that are present in the same location as defect 608 in other reticle fields are not detected (e.g., due to the tower signal of defects 616 and 618). When the results of the die-to-die comparisons are input to repeater algorithm 620, therefore, random defects 610, 612, and 614 will be identified as non-repeating defects and eliminated from inspection results 622. However, the repeater algorithm will also eliminate defect 608 from the inspection results since defects were not detected at the same location as defect 608 within multiple reticle fields.

Figure 7:
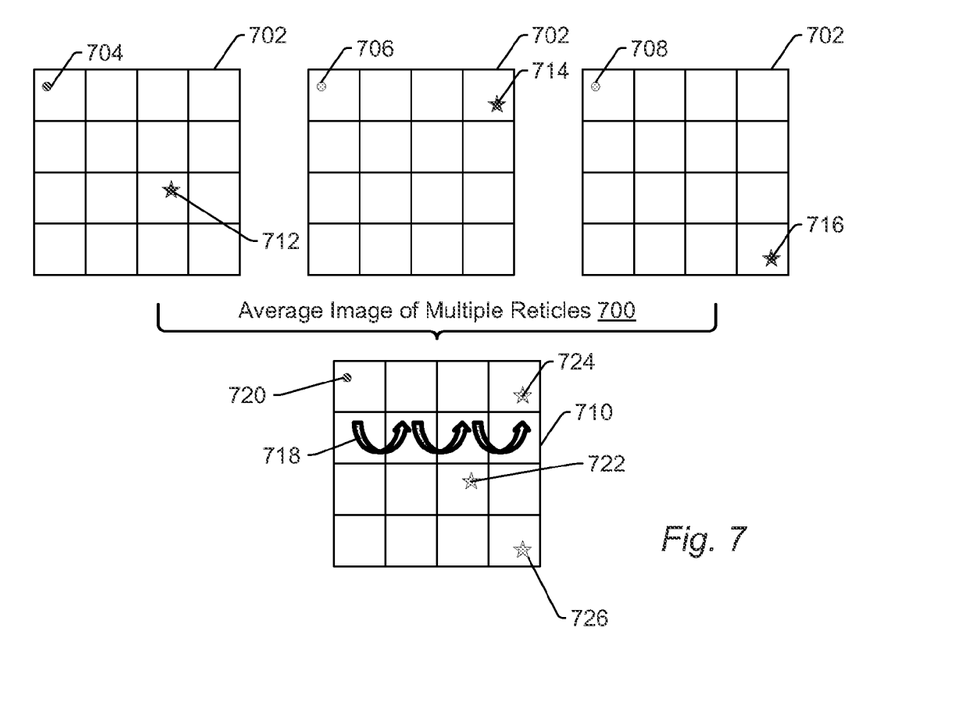
FIG. 7 is a schematic diagram illustrating one embodiment of a method for detecting defects on a wafer.

In contrast, in the embodiments described herein for repeater in random or RIR inspection, the computer subsystem is configured to average images of multiple reticles, as shown by step 700 in FIG. 7, to thereby generate average image 710 of reticle 702. For example, one embodiment of a system configured to detect defects on wafers includes an inspection subsystem configured to scan a wafer to thereby generate images for the wafer. The inspection subsystem may include any of the inspection subsystems described further herein. Two or more reticle fields are printed on the wafer, and each of the two or more reticle fields includes two or more dies printed on the wafer. For example, as shown in FIG. 6, reticle fields 604, each of which include dies 602, may be printed on a wafer. The computer subsystem, which may include any of the computer subsystems described herein, is configured for generating one or more test images for at least one of the two or more dies by averaging two or more of the images generated in the at least one die in two or more of the reticle fields, in one embodiment, the averaging includes a robust averaging, which may be performed as described further herein. Averaging the images of the multiple reticle fields will reduce the signal of any defects that are not located in substantially the same location in the multiple reticle fields. For example, as shown in FIG. 7, defects 712, 714, and 716 that do not repeat in multiple reticle fields will produce a signal at the location of these defects in averaged image 710 that is less than the signal for each of these defects.

In this manner, defect detection performed on the averaged image will be able to detect more repeating defects and fewer defects. Defect detection that is performed on the averaged image may include any suitable defect detection known in the art such as die-to-die comparisons 718. For example, in one embodiment, the computer subsystem is further configured for determining one or more difference images for the at least one die by subtracting one or more test images for another die on the wafer from the one or more test images for the at least one die and detecting defects on the wafer based on the one or more difference images. Such defect detection may detect defect 720 corresponding to repeating defects 704, 706, and 708 and may not detect defects 722, 724, and 726 that correspond to defects 712, 714, and 716. In this manner, in some embodiments, the defects that are detected in the detecting step include repeating defects. Therefore, the defect detection will detect repeating defects but not non-repeating or random defects. As such, this defect detection can increase the sensitivity of inspection for smaller and/or lower signal repeaters.

In one embodiment, the defects include repeating defects, and the computer subsystem is configured for determining if the defects are due to defects on a reticle used to print the wafer. Determining if the defects on the wafer are due to defects on the reticle used to print the wafer may be performed as described further herein.

The embodiments described herein have a number of advantages over other methods and systems for wafer inspection. For example, compared to currently used die-to-die comparisons, RIR is able to remove random wafer noise/nuisance by averaging reticle images and increasing the signal-to-noise ratio of reticle defects that will be repeaters. In other words, the RIR described herein makes the background quieter and enhances detection of repeater defects. In addition, the embodiments described herein address the sensitivity of repeater detection in the random regions of wafers. For example, in one embodiment, the generating, determining, and detecting steps are performed for only logic regions in the two or more dies. Compared to the embodiments described herein for array region inspection, RIR includes reticle-to-reticle alignment and image recording during inspection.

Further modifications and alternative embodiments of various aspects of the invention will be apparent to those skilled in the art in view of this description. For example, systems and methods for detecting defects on a wafer are provided. Accordingly, this description is to be construed as illustrative only and for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to detect defects on a wafer, comprising:
    an inspection subsystem configured to scan a wafer to thereby generate frame images for the wafer, wherein the inspection subsystem comprises at least a light source and one or more detectors, wherein the inspection subsystem is further configured to direct light from the light source to the wafer, and wherein light from the wafer is collected and detected by the one or more detectors of the inspection subsystem during scanning to thereby generate the frame images; and
    a computer subsystem configured for:
        generating one or more test images for at least a portion of an array region in one or more dies on the wafer from one or more of the frame images;
        generating a reference image for one or more cells in the array region from two or more of the frame images;
        determining one or more difference images for at least one cell in at least the portion of the array region in the one or more dies by subtracting the reference image from one or more portions of the one or more test images corresponding to the at least one cell; and
        detecting defects on the wafer in the at least one cell based on the one or more difference images determined for the at least one cell, wherein the defects comprise repeating defects.

2. The system of claim 1, wherein the light source comprises a broadband plasma light source.

3. The system of claim 1, wherein the inspection subsystem is further configured as a bright field tool.

4. The system of claim 1, wherein the computer subsystem is further configured for determining if the repeating defects are due to haze on a reticle used to print the wafer.

5. The system of claim 1, wherein the computer subsystem is further configured for generating the one or more test images by combining at least two of the frame images corresponding to the same locations in the one or more dies thereby creating additional image data for the wafer, and wherein the additional image data is used as the one or more test images in said determining one or more difference images.

6. The system of claim 5, wherein the at least two of the frame images comprise images of at least two of the one or more dies.

7. The system of claim 5, wherein the at least two of the frame images comprise images of at least two reticle fields printed on the wafer.

8. The system of claim 5, wherein the computer subsystem is further configured for performing said detecting using a predetermined threshold at a noise floor of output of a detector of the inspection subsystem.

9. A system configured to detect defects on a wafer, comprising:
an inspection subsystem configured to scan a wafer to thereby generate images for the wafer, wherein the inspection subsystem comprises at least a light source and one or more detectors, wherein the inspection subsystem is further configured to direct light from the light source to the wafer, and wherein light from the wafer is collected and detected by the one or more detectors of the inspection subsystem during scanning to thereby generate the images; and
a computer subsystem configured for:
while the inspection subsystem is scanning the wafer, detecting defects on the wafer by applying a predetermined threshold to the images, wherein the predetermined threshold is at a noise floor of output of a detector included in the one or more detectors of the inspection subsystem;
while the inspection subsystem is scanning the wafer, combining results of said detecting corresponding to the same locations in two or more dies or two or more reticle fields on the wafer;
while the inspection subsystem is scanning the wafer, identifying one set of the defects that is detected at all of the same locations as repeating defects;
while the inspection subsystem is scanning the wafer, identifying another set of the defects that is detected at fewer than all of the same locations as non-repeating defects; and
generating inspection results for the wafer that comprise information for at least the repeating defects.

10. The system of claim 9, wherein the light source comprises a broadband plasma light source.

11. The system of claim 9, wherein the inspection subsystem is further configured as a bright field tool.

12. The system of claim 9, wherein the computer subsystem is further configured for performing said combining for only array regions of the two or more dies or the two or more reticle fields.

13. The system of claim 9, wherein the computer subsystem is further configured for determining if the repeating defects comprise two or more defects formed on the wafer due to haze on a reticle used to print the wafer.

14. The system of claim 9, wherein the computer subsystem is further configured for performing, said generating the inspection results by excluding information for the non-repeating defects from the inspection results.

15. The system of claim 9, wherein the computer subsystem is further configured for applying a nuisance filter to the non-repeating defects to identify at least one of the non-repeating defects that is an actual defect and at least one other of the non-repeating defects that is a nuisance.

16. A system configured to detect defects on a wafer, comprising:
an inspection subsystem configured to scan a wafer to thereby generate images for the wafer, wherein the inspection subsystem comprises at least a light source and one or more detectors, wherein the inspection subsystem is further configured to direct light from the light source to the wafer, wherein light from the wafer is collected and detected by the one or more detectors of the inspection subsystem during scanning to thereby generate the images, wherein two or more reticle fields are printed on the wafer, and wherein each of the two or more reticle fields comprises two or more dies printed on the wafer; and
a computer subsystem configured for:
generating one or more test images for at least one of the two or more dies by averaging two or more of the images generated in the at least one die in two or more of the reticle fields;
generating one or more test images for another die on the wafer from two or more of the images generated in the other die in the two or more of the reticle fields;
determining one or more difference images for the at least one die by subtracting the one or more test images for the other on the wafer from the one or more test images for the at least one die; and
detecting defects on the wafer based on the one or more difference images.

17. The system of claim 16, wherein the computer subsystem is further configured to perform the averaging by performing a robust averaging.

18. The system of claim 16, wherein the computer subsystem is further configured for performing said generating, determining, and detecting only for logic regions in the two or more dies.

19. The system of claim 16, wherein the computer subsystem is further configured for determining if the defects comprise repeating defects.

20. The system of claim 16, wherein the defects comprise repeating defects, and wherein the computer subsystem is further configured for determining if the repeating defects are due to defects on a reticle used to print the wafer.

21. The system of claim 16, wherein the light source comprises a broadband plasma light source.

22. The system of claim 16, wherein the inspection subsystem is further configured as a bright field tool.

* * * * *